(12) United States Patent
Brinkman (10) Patent No.: US 10,120,179 B2
(45) Date of Patent: Nov. 6, 2018

(54) INVERTED MICROSCOPE AND INVERTED MICROSCOPE SYSTEM

(71) Applicant: OLYMPUS CORPORATION, Hachioji-shi, Tokyo (JP)

(72) Inventor: Brendan Brinkman, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/217,267

(22) Filed: Jul. 22, 2016

(65) Prior Publication Data

US 2017/0031150 A1 Feb. 2, 2017

(30) Foreign Application Priority Data

Jul. 31, 2015 (JP) ................. 2015-152139

(51) Int. Cl.
| | |
|---|---|
| G02B 21/26 | (2006.01) |
| G02B 21/33 | (2006.01) |
| G02B 21/00 | (2006.01) |
| G02B 21/24 | (2006.01) |
| G01N 21/25 | (2006.01) |
| G01N 21/03 | (2006.01) |

(52) U.S. Cl.
CPC ........... *G02B 21/33* (2013.01); *G01N 21/253* (2013.01); *G02B 21/0088* (2013.01); *G02B 21/24* (2013.01); *G02B 21/26* (2013.01); *G01N 2021/0357* (2013.01)

(58) Field of Classification Search
CPC ......... G01N 2021/0357; G01N 21/253; G02B 21/0088; G02B 21/24; G02B 21/26; G02B 21/33

USPC ........................................................ 359/393
See application file for complete search history.

(56) References Cited

U.S. PATENT DOCUMENTS

| 5,870,223 | A | * | 2/1999 | Tomimatsu | .............. | G02B 1/06 |
|---|---|---|---|---|---|---|
| | | | | | | 359/392 |
| 6,980,293 | B1 | | 12/2005 | Harada | | |
| 7,602,494 | B2 | * | 10/2009 | Harada | .................. | G02B 21/16 |
| | | | | | | 356/317 |

(Continued)

FOREIGN PATENT DOCUMENTS

| JP | 4328359 B2 | 9/2009 |
|---|---|---|
| JP | 4443832 B2 | 3/2010 |

OTHER PUBLICATIONS

Extended European Search Report (EESR) dated Dec. 16, 2016, issued in counterpart European Patent Application No. 16181212.8.

*Primary Examiner* — Collin X Beatty
(74) *Attorney, Agent, or Firm* — Holtz, Holtz & Volek PC (57) ABSTRACT

This inverted microscope comprises the following elements: an immersion objective lens, a medium container which is disposed above the immersion objective lens with a gap, and which has a bottom surface having a transparent portion and being capable of retaining a first immersion medium between the transparent portion and the immersion objective lens, and also which is capable of storing inside thereof a second immersion medium having a refractive index which is the same as or similar to that of the first immersion medium; and a movable stage to support a sample container, which accommodates a specimen, in a horizontally movable manner inside the medium container and which has a transparent portion in at least a part of a bottom surface thereof.

11 Claims, 8 Drawing Sheets

(56) References Cited

U.S. PATENT DOCUMENTS

| | | | |
|---|---|---|---|
| 8,482,854 B2 * | 7/2013 | Lippert | G02B 21/26 |
| | | | 359/381 |
| 2004/0263961 A1 | 12/2004 | Hummel | |
| 2008/0170292 A1 | 7/2008 | Harada et al. | |
| 2008/0246972 A1 * | 10/2008 | Dubois | G01B 9/02057 |
| | | | 356/521 |
| 2009/0086314 A1 | 4/2009 | Namba et al. | |
| 2016/0139394 A1 * | 5/2016 | Taniguchi | G02B 21/24 |
| | | | 359/385 |

* cited by examiner

INVERTED MICROSCOPE AND INVERTED MICROSCOPE SYSTEM

CROSS-REFERENCE TO RELATED APPLICATIONS

This application is based on Japanese Patent Application No. 2015-152139 filed on Jul. 31, 2015, the contents of which are incorporated herein by reference.

TECHNICAL FIELD

The present invention relates to an inverted microscope and an inverted microscope system.

BACKGROUND ART

Conventionally, an inverted microscope equipped with a supply means for supplying immersion liquid as the immersion medium between a container containing a specimen and an objective lens which is brought close to the lower side of the container is known. (See PTL 1, for example.)

CITATION LIST

Patent Literature

{PTL 1} Japanese Patent No. 4443832

SUMMARY OF INVENTION

An aspect of the present invention is to provide an inverted microscope comprising: an immersion objective lens, a medium container which is disposed above the immersion objective lens with a gap, and which has a bottom surface having a transparent portion and being capable of retaining a first immersion medium between the transparent portion and the immersion objective lens, and also which is capable of storing inside thereof a second immersion medium having a refractive index which is the same as or similar to that of the first immersion medium; and a movable stage to support a sample container, which accommodates a specimen, in a horizontally movable manner inside the medium container and which has a transparent portion in at least a part of a bottom surface thereof.

DESCRIPTION OF EMBODIMENTS

An inverted microscope 2 and an inverted microscope system 1 according to an embodiment of the present invention are described below with reference to the drawings.

Figure 1:
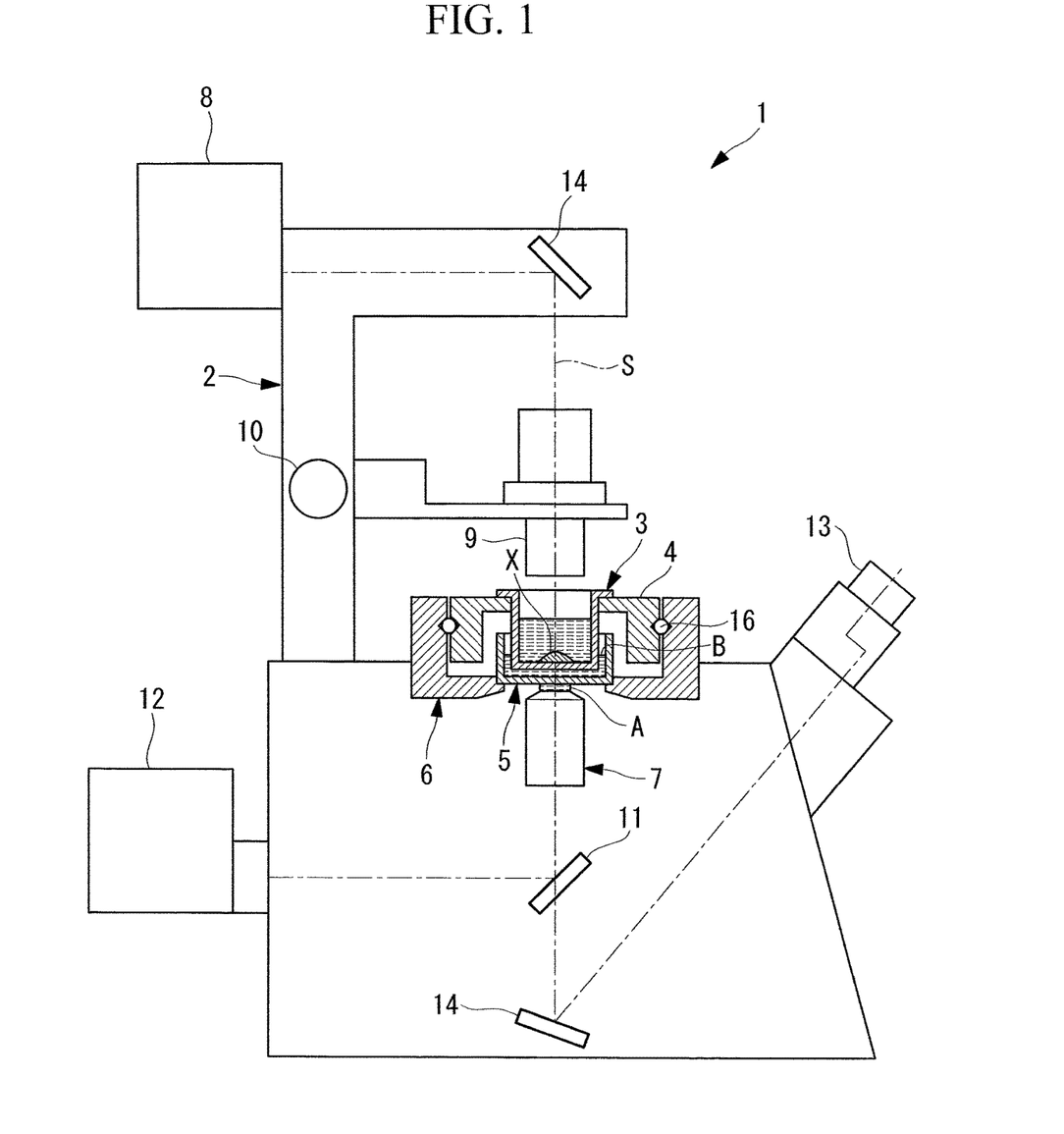
FIG. 1 is a drawing showing a whole structure of an inverted microscope system according to a first embodiment of the present invention.

As shown in FIG. 1, the inverted microscope system 1 according to the embodiment has the inverted microscope 2 according to the embodiment of the present invention for observation of a specimen X, and a sample container 3 which accommodates the specimen X and which is supported by the inverted microscope 2.

The inverted microscope 2 of this embodiment has a movable stage 4 for supporting the sample container 3 for accommodating the specimen X, a medium container 5 located at a position so that the medium container 5 accommodates the sample container 3 which is supported by the movable stage 4, a fixed stage (container stage) 6, and an immersion objective lens disposed right below the medium container 5 with a gap.

In the drawings, the reference sign 8 indicates a light source, the reference sign 9 indicates a condenser lens, the reference sign 10 indicates a handle for moving the condenser lens in a vertical direction, the reference sign 11 indicates a half mirror, the reference sign 12 indicates a camera, the reference sign 13 indicates an eyepiece, and the reference sign 14 indicates a mirror.

Figure 3A:
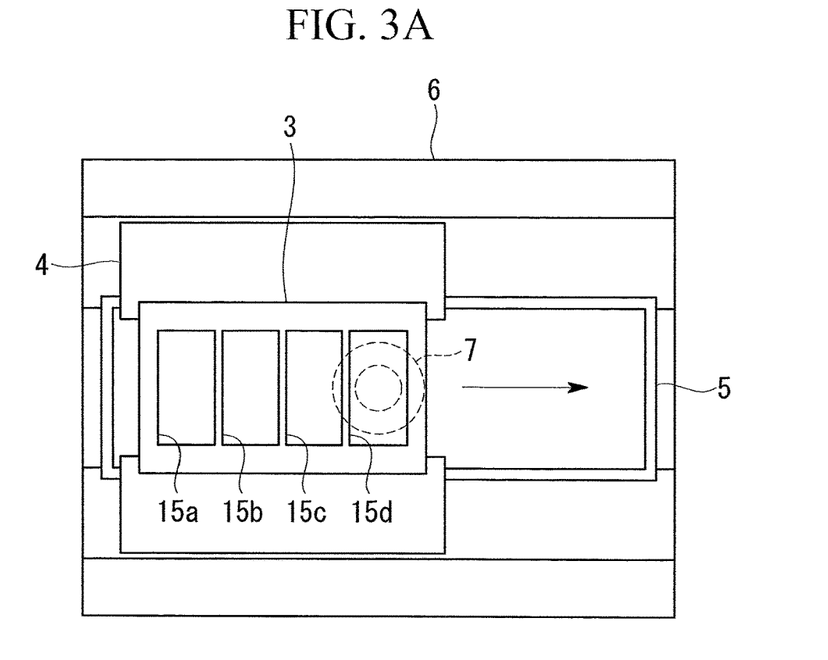
FIG. 3A is a plane view which shows a state in which a movable stage is moved to one end of a movable range of a sample container attached to the movable stage of the inverted microscope system shown in FIG. 1.
Figure 3B:
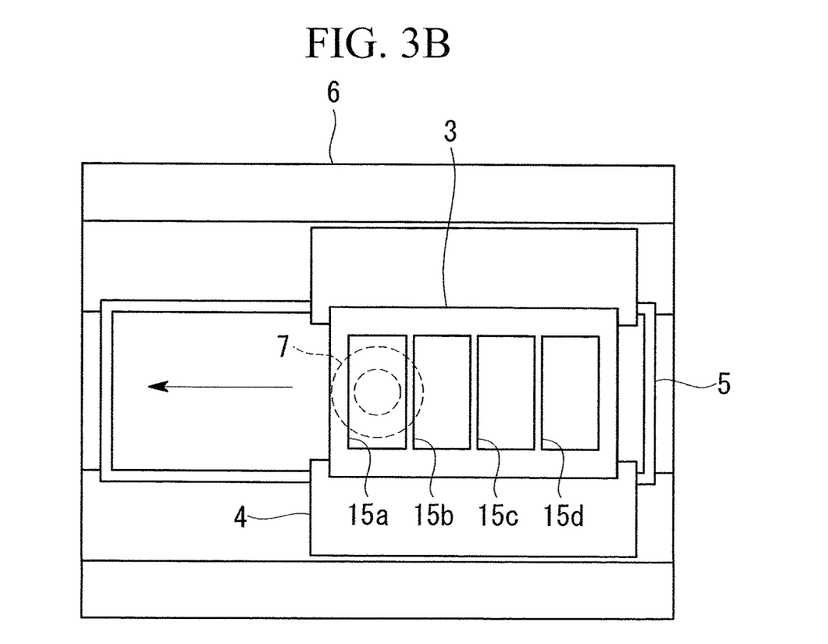
FIG. 3B is a plane view which shows a state in which a movable stage is moved to the other end of the movable range of a sample container attached to the movable stage of the inverted microscope system shown in FIG. 1.

As shown in FIG. 3, the sample container is a multi-well container which has 4 wells 15a, 15b, 15c, 15d arranged on a straight line and which has a rectangular parallelepiped box-shape, and each of the wells 15a, 15b, 15c, 15d accommodates a specimen X. At least the bottom of each well 15a, 15b, 15c, 15d are made of an optically transparent material. As the specimen X, any kind of the cells that grow in an adhered state on the bottom surface of the wells 15a, 15b, 15c, 15d can be used.

The medium container 5 has an optically transparent portion in at least part of the bottom surface 5b, and has an opening portion 5a which opens upward when the medium container is positioned so that the bottom surface 5b is located at the lower side of the container. The width of the medium container 5 is larger than the width of the sample container 3, and the length of the medium container 5 is as approximately two times long as the width of the sample container 3.

Figure 2:
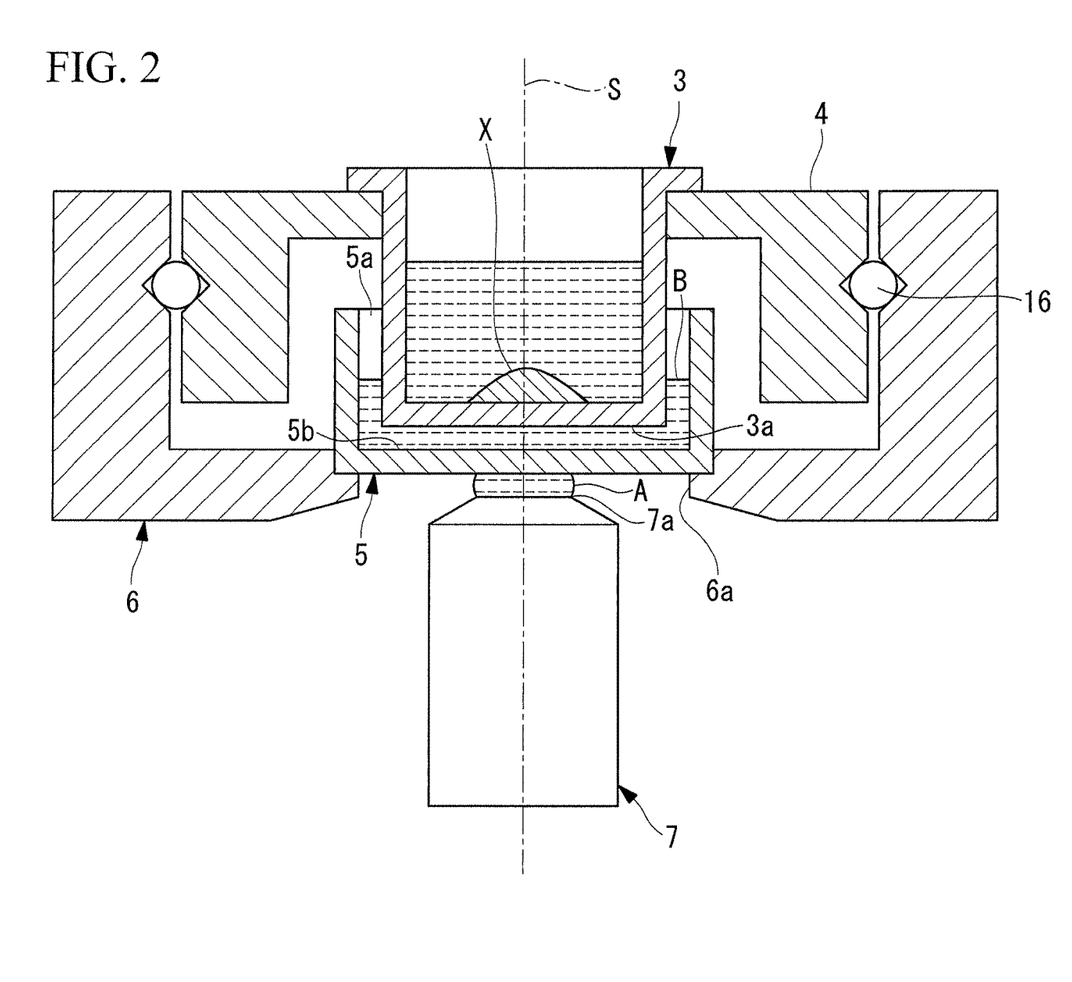
FIG. 2 is a partial longitudinal sectional view showing an adjacent part of an immersion objective lens of the inverted microscope system shown in FIG. 1.

As shown in FIG. 2, the medium container 5 is mounted on the fixed stage 6 so that the opening portion 5a is positioned at the upper side of the container and the bottom surface 5b becomes substantially horizontal, and immersion liquid (second immersion medium) B is accommodated in the container.

The fixed stage 6 has an opening portion 6a which is provided at a position corresponding to the substantially middle portion of the mounted medium container 5 and which allows the bottom surface 5b to be exposed below.

As shown in FIG. 2, the movable stage 4 is configured so that the longitudinal direction of the sample container 3 is consistent with the longitudinal direction of the medium container 5 when the sample container 3 is mounted on the movable stage 4. Further, the sample container 3 mounted on the movable stage 4 is configured so that the bottom surface 3a thereof is accommodated in the medium container 5 and positioned above the bottom surface 5b of the medium container 5 forming a gap, and that the bottom surface 3a is immersed in the immersion liquid A stored in the medium container 5. With this configuration, the immersion liquid B is filled in the gap between the bottom surface 5b of the medium container 5 and the bottom surface 3a of the sample container 3.

Also, the movable stage 4 is configured to move the sample container 3 in the medium container 5 along the horizontal direction and along the longitudinal direction of the sample container 3 and the medium container 5. In the drawings, the reference sign 16 indicates a bearing which supports the movable stage 4 in such a manner that the movable stage 4 can move relative to the fixed stage 6 and along a straight track extending in the horizontal direction. The movable stage 4 is voluntarily moved to a horizontal position by a linear motion mechanism such as a motor and a ball screw, or etc., which are not shown in the drawings. Note that the movable stage 4 can be configured so as to be manually moved.

As shown in FIG. 2, the immersion objective lens 7 is disposed upward so that the optical axis S is positioned at a position which is consistent with the opening 6a of the fixed stage 6 and the optical axis S is disposed vertically. The immersion objective lens 7 can hold the immersion liquid (first immersion medium) A, with surface tension, between the tip lens 7a and the bottom surface 5b of the medium container 5 exposed from the opening 6a.

With this configuration, the bottom surface 3a of the sample container 3, the bottom surface 5b of the medium container 5, and the immersion liquid B which is filled in the gap therebetween fill the space between the immersion objective lens 7 and the specimen X. The bottom surface 3a of the sample container 3, the bottom surface 5b of the medium container 5, and the immersion liquid B are made of a material or materials which has or have a refractive index which is equivalent to the specimen X. With this configuration, the light from the specimen X of the sample container 3 is not refracted at each interface, and is condensed by the immersion objective lens 7.

A function of the inverted microscope 2 and the inverted microscope system 1 configured as described above will be explained below.

In order to observe a specimen X using the inverted microscope system 1 according to this embodiment, the medium container 5, in which the immersion liquid B is accommodated, is fixed to the fixed container 6, and the sample container 3, which accommodates specimens X in the wells 15a, 15b, 15c, 15d, is attached to the movable stage 4.

By the aforementioned steps, the entire bottom surface 5b of the sample container 3 is immersed in the immersion liquid B accommodated in the medium container 5.

At this stage, since the immersion objective lens 7 is disposed below the substantially middle portion of the bottom surface 5b of the medium container 5 forming a gap, the immersion liquid B is held in the gap between the tip lens 7a of the immersion objective lens 7 and the bottom surface 5b of the medium container 5. By this configuration, the light from the specimen X is condensed by the immersion objective lens 7 and then observed.

With the inverted microscope system 1 according to this embodiment, by using the immersion objective lens 7 which has a numerical aperture greater than a dry objective lens, high resolution microscope images can be obtained. Further, in a case where the inside of a 3 dimensional cell culture as spheroids is observed, it is possible to suppress the generation of optical aberration by reducing the difference between the refractive index of the cell and the surrounding materials, which affords an advantage of obtaining clear images.

Also, in order to observe the specimens X in the respective wells 15a, 15b, 15c, 15d, the movable stage 4 is moved in the horizontal direction relative to the fixed stage 6 by the pitch of the wells 15a, 15b, 15c, 15d. By this, the sample container 3 is moved in the horizontal direction in the medium container 5, the bottom surface of the next well 15a, 15b, 15c, 15d is positioned on the optical axis S of the immersion objective lens 7, and then it becomes possible to observe the specimen X accommodated in the wells 15a, 15b, 15c, 15d. The specimen X accommodated in the further next well can be observed in order by moving the movable stage 4.

In this case, the sample container 3 is moved in the state in which the bottom surface 3a thereof is immersed in the immersion liquid B, the state in which the immersion liquid B is filled between the bottom surface 5b of the medium container 5 and the bottom surface 3a is maintained. Also, when the sample container 3 is moved, the medium container 5 does not move relative to the immersion objective lens 7. Therefore, gap between the medium container 5 and the immersion objective lens 7 is kept filled by the immersion liquid A.

Thus, with the inverted microscope system 1 according to this embodiment, when the position of the specimen X is changed, the immersion liquid A which is held on the tip lens 7a of the immersion objective lens 7 is not forced to move, and therefore an advantage of preventing liquid shortage is achieved. Further, when the sample container 3 moves relative to the medium container 5 by the movement of the movable stage 4, since the sample container 3 moves in the immersion liquid B stocked in the medium container 5, liquid shortage does not occur by the movement.

As described above, with the inverted microscope system 1 according to this embodiment, liquid shortage does not occur by moving the immersion liquid B, it is not necessary to replenish the immersion liquid B frequently. Therefore, it is possible to reduce consumption of the immersion liquid B, and therefore to reduce the costs, which are advantages of this embodiment. Further, it is possible to shorten the time for replenishment of the immersion liquid B, and therefore to shorten the observation time, which are also advantages of this embodiment.

Although the case in which the multi-well container having the wells 15a, 15b, 15c, 15d is used as the sample container 3 is illustrated in this embodiment, it is possible to employ a sample container 3 which does not have the wells 15a, 15b, 15c, 15d, but has a flat bottom area which exceeds the field of view area of the immersion objective lens 7. In this case, it is also necessary to move the sample container 3 in the direction perpendicular to the light axis S of the immersion objective lens 7 in order to observe the specimens which are disposed at the respective positions on the bottom surface 3a, and therefore the same or a similar effect can be achieved.

Also, the sample container 3 is moved relative to the medium container 5 toward one direction in the horizontal direction by moving the movable stage 4 relative to the fixed stage 6 in this embodiment, it is also possible to move the sample container 3 in a two dimensional direction, or in a three dimensional direction including a vertical axis.

Figure 7:
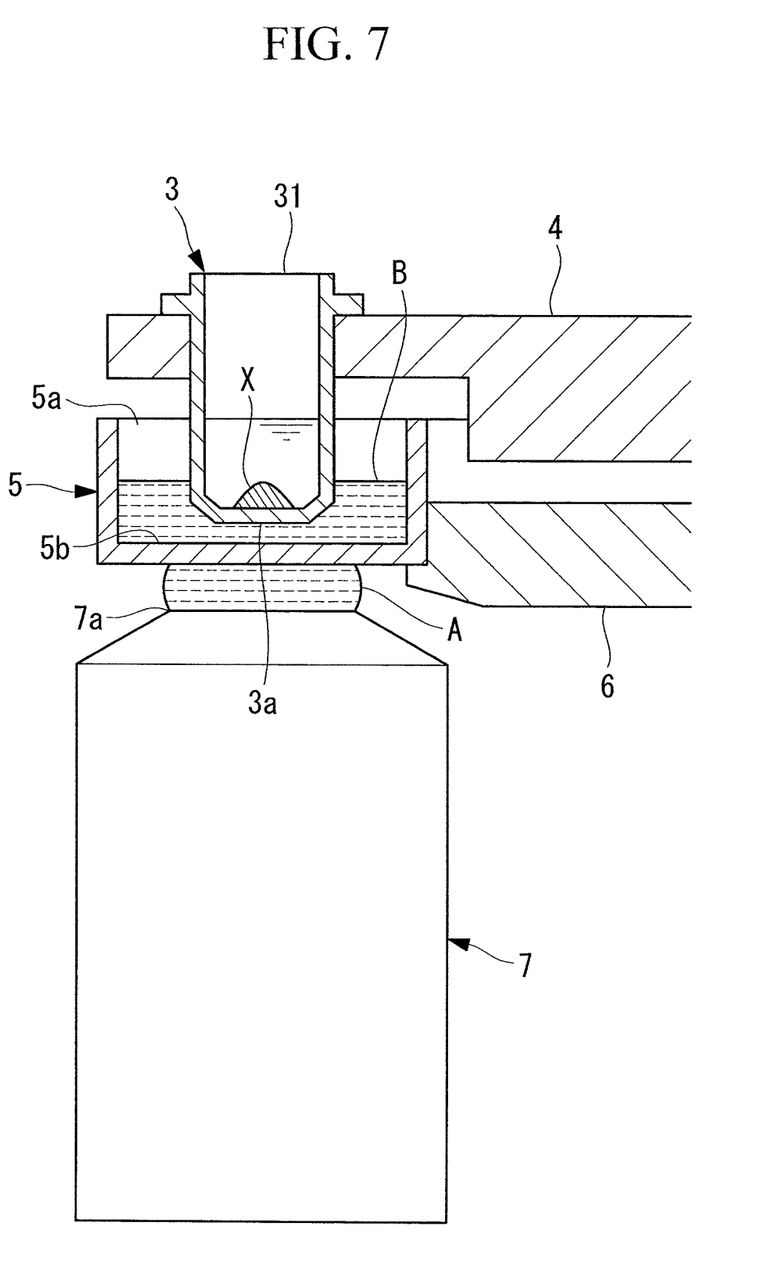
FIG. 7 is a partial longitudinal sectional view showing a modified example in which the sample container of FIG. 6 is replaced with cuvettes.

In addition, a single multi-well container having the plurality of wells 15a, 15b, 15c, 15d is employed as the sample container 3, the sample container 3 may be composed of a plurality of cuvettes 31 supported in an aligned state in the moving direction of the movable stage 4 as shown in FIG. 7.

Figure 8:
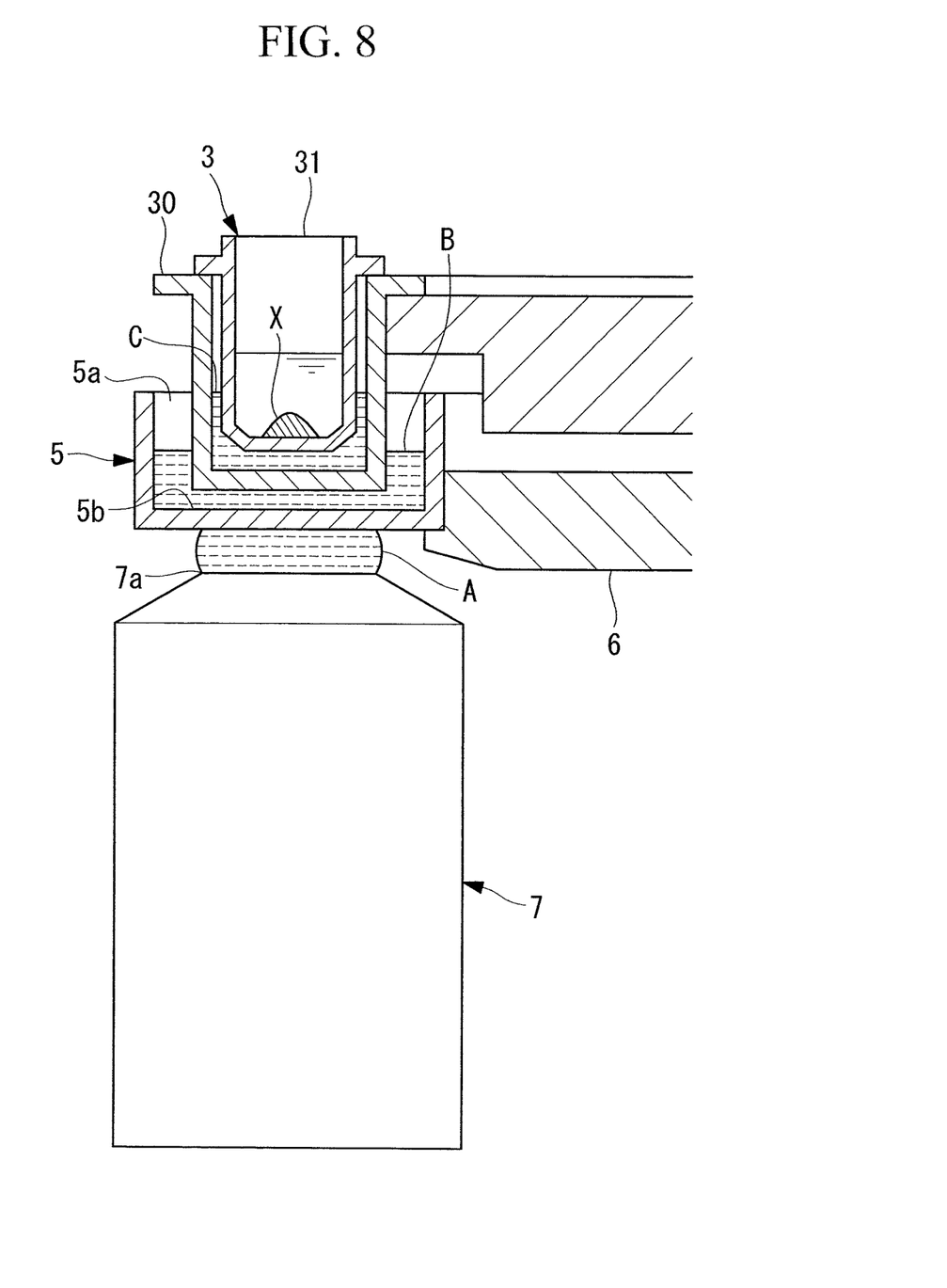
FIG. 8 is a partial longitudinal sectional view showing a modified example in which the sample container is replaced with a multi-well container having a plurality of cuvettes that are inserted in the wells, respectively.

Further, it is also possible to accommodate the immersion liquid (third immersion medium) C in each of the wells of a multi-well container, and to insert the cuvettes 31, each of which accommodates the specimen X, into the respective wells as shown in FIG. 8.

Figure 4:
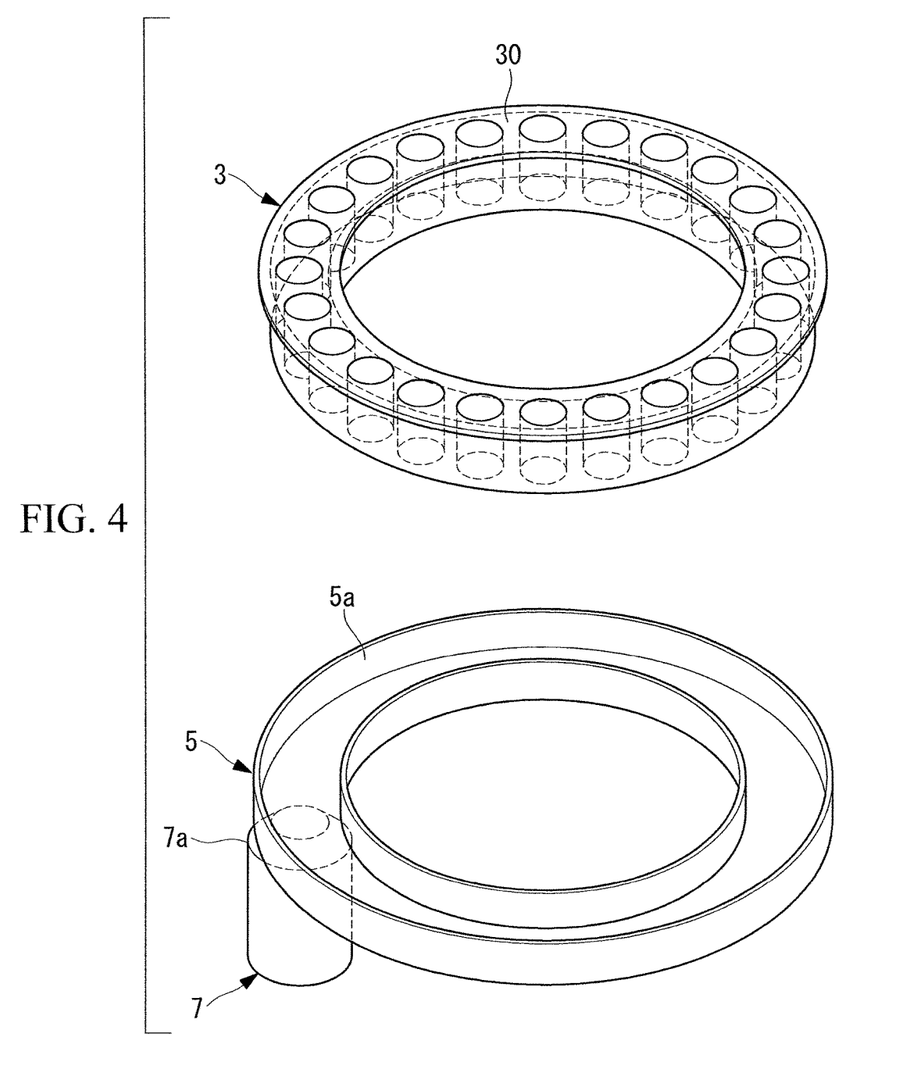
FIG. 4 is an exploded perspective view showing a sample container, a medium container, and an immersion objective lens of a modified example of the inverted microscope system shown in FIG. 1.

Also, in this embodiment, the annulus-shape medium container as shown in FIG. 4 can be employed as the medium container 5. In this case, as the sample container 3 accommodated in the medium container 5, the system can use a sample container which accommodates a plurality of specimens X at the different positions in the circumferential direction of the medium container 5, such as the following ones: the annulus-shape multi-well container as shown in FIG. 4; an arc-shape multi-well container (not shown in the drawings) as part of the annulus ape multi-well container; an annulus-shape or arc-shape sample container which does not have the wells 15a, 15b, 15c, 15d; or a sample container 3 which is composed of a plurality of cuvettes 31 arranged in an arc state or a circumferential state.

Figure 5:
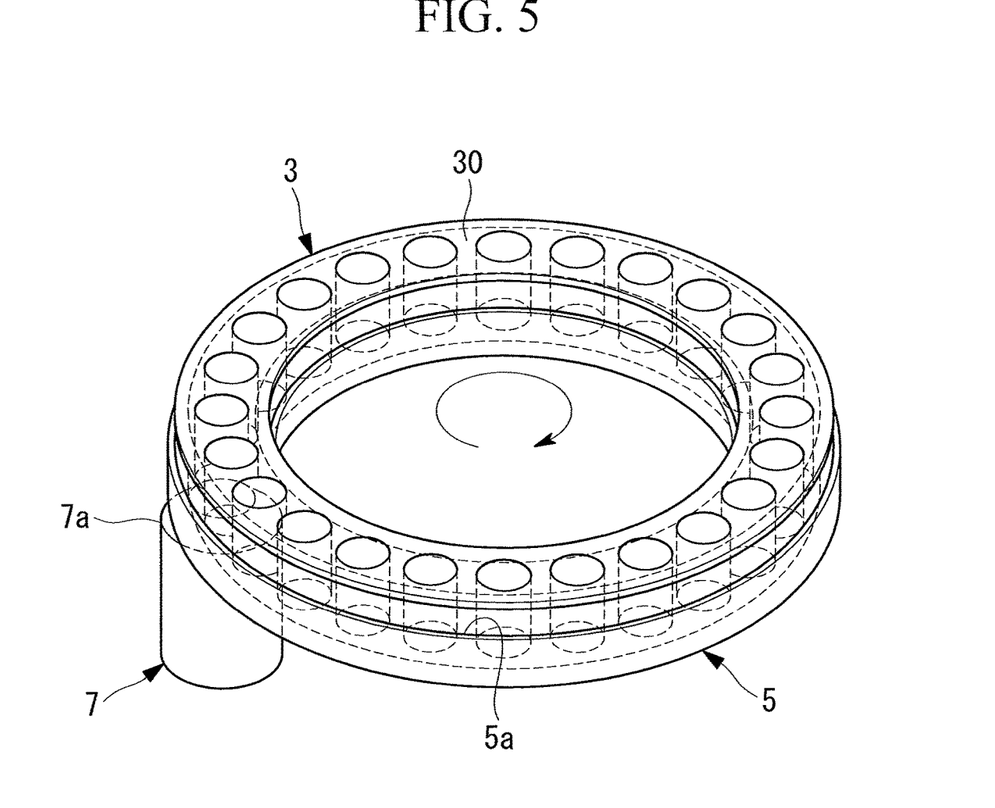
FIG. 5 is a perspective view showing a state in which the sample container is accommodated in the medium container.
Figure 6:
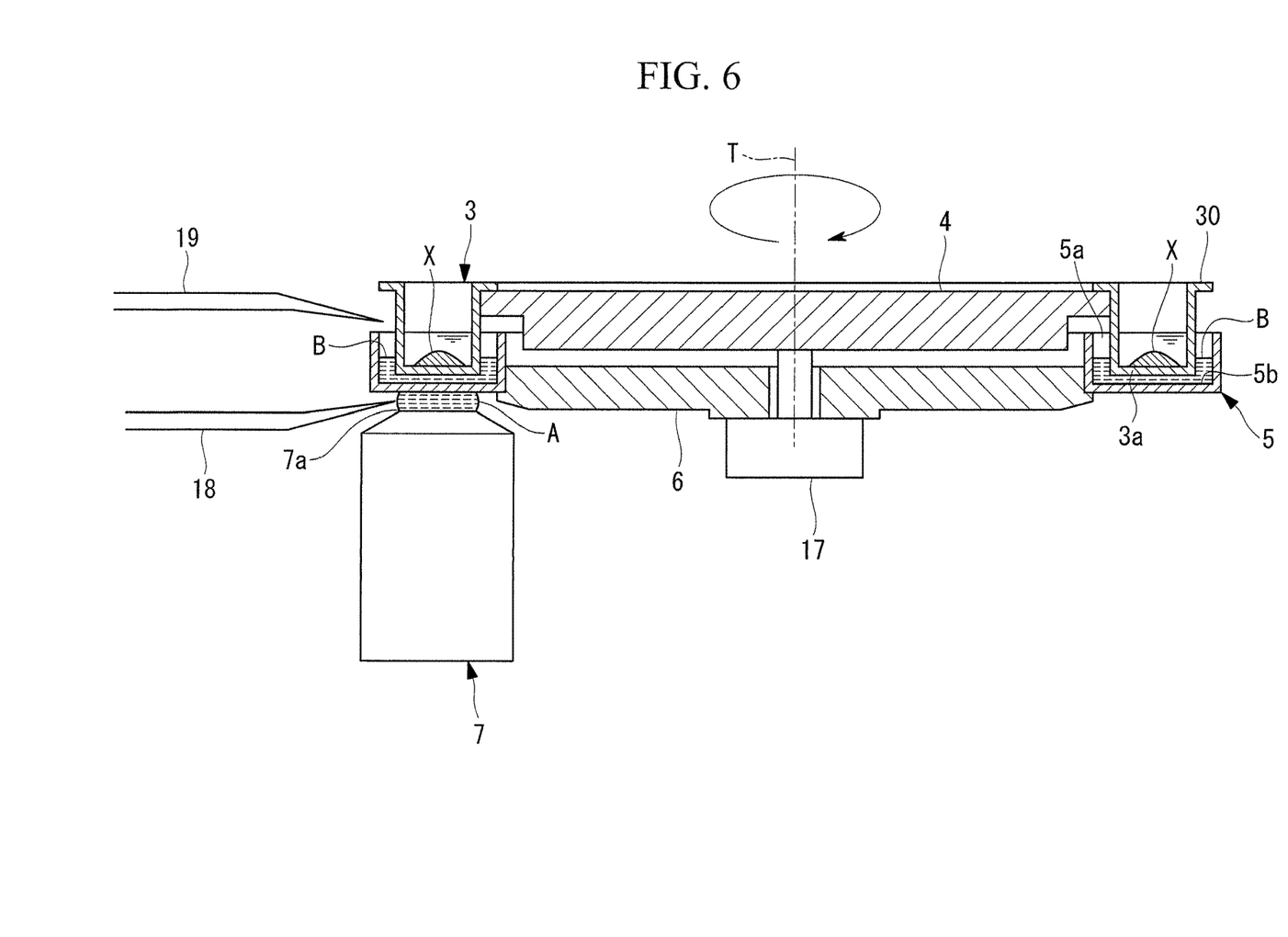
FIG. 6 is a longitudinal sectional view showing a state in which the sample container, the sample container, and the immersion objective lens shown in FIG. 5 are assembled.

Also, in this case, the immersion objective lens 7 is stationary relative to an XY position of the bottom surface 5b of the medium container 5 so that the optical axis S thereof is consistent with a predetermined circumferential position of the bottom surface 5b as shown in FIGS. 5 and 6. Also, as shown in FIG. 6, the movable stage 4 for moving the sample container 3 has a motor 17 which rotates the sample container 3 around an axis which is consistent with the center axis (vertical axis) of the medium container 5.

With the inverted microscope system 1 configured as described above, when the motor rotates the movable stage 4, the sample container 3 supported by the movable stage 4 moves in the circumferential direction in the medium container 5, the specimens X which are located at the different positions or in the different wells or cuvettes are sequentially arranged on the optical axis S of the immersion objective lens 7. By forming the medium container 5 in an annulus shape, it becomes possible to repeatedly observe all the specimens X without reciprocating movement, by moving the movable stage 4 toward one direction, which is one of the advantages.

Also, even in the inverted microscope system 1 according to this embodiment, since the immersion liquid B in the medium container 5 and the immersion liquid A between the medium container 5 and the immersion objective lens 7 decrease naturally by evaporation or the like, a supply device including nozzles (first medium supply portion, second medium supply portion) 18, 19 may be employed as shown in FIG. 6. The reduced amount of the immersion liquid A naturally reduced by evaporation or the like is sufficiently smaller than the reduced amount of the immersion liquid B reduced by moving the immersion liquid B, and therefore frequent supply of the immersion liquid is not required.

Although the medium container 5 and the immersion objective lens 7 are mutually fixed in this embodiment, a configuration in which the medium container 5 is moved relative to the immersion objective lens 7 toward a direction perpendicular to the moving direction of the sample container 3 by the movable stage 4 can be employed. For example, when the movable stage 4 moves along a straight line as shown in FIG. 3, the fixed stage 6 may be moved toward a direction perpendicular to the straight line.

As shown in FIG. 6, in a case where the movable stage 4 rotates around the center axis line T, a configuration in which the fixed stage 6 which supports the medium container 5 is moved toward the radial direction may be employed.

Although the immersion liquid is moved when the medium container 5 is moved relative to the immersion objective lens 7, by limiting the amount of movement, it becomes possible to prevent the liquid shortage by moving the medium container 5, and also to easily broaden the observation area, which are advantages of this embodiment.

Further, in this embodiment, it is also possible to provide a controller (not shown in the drawings) to control the motor 17 to move the movable stage 4 so that one of the wells 15a, 15b, 15c, 15d of the multi-well container 3 or one of the plurality of cuvettes 31 is positioned on the optical axis S of the immersion observation lens 7.

An aspect of the present invention which includes the aforementioned embodiment is to provide an inverted microscope comprising: an immersion objective lens, a medium container which is disposed above the immersion objective lens with a gap, and which has a bottom surface having a transparent portion and being capable of retaining a first immersion medium between the transparent portion and the immersion objective lens, and also which is capable of storing inside thereof a second immersion medium having a refractive index which is the same as or similar to that of the first immersion medium; and a movable stage to support a sample container, which accommodates a specimen, in a horizontally movable manner inside the medium container and which has a transparent portion in at least a part of a bottom surface thereof.

According to this aspect, the observation of the specimen through the immersion objective lens is performed in a state in which at least the bottom surface of the sample container for accommodating the specimen is soaked in the second immersion medium in the medium container which accommodates the second immersion medium, and in which the first immersion medium is retained between the bottom surface of the medium container and the immersion objective lens which is located near the lower side of the medium container. Since the space between the immersion objective lens and the specimen is filled with the sample container, the medium container, and the first and second immersion medium positioned therebetween, and each of which has a refractive index that is the same as or similar to those of the others, it is possible to obtain high resolution microscope images by using an immersion objective lens which has a numerical aperture greater than a dry objective lens.

In this case, when the specimens located at the different positions in the sample container are observed, the sample container is horizontally moved in the medium container by operating the movable stage. When the sample container is horizontally moved relative to the medium container, the state in which the gap between the both containers is filled with the second immersion medium is kept unchanged. Further, since the medium container is not moved relative to the immersion objective lens, the first immersion medium that fills the space therebetween is not largely reduced. Therefore, when the sample container is moved to observe the specimens that are placed at the different positions, it is possible to perform a stable observation for a long time period, preventing liquid shortage of the immersion medium, without a frequent supply of the medium. Further, it is possible to reduce the amount of immersion medium to be stocked, and then to reduce the frequency of the supply work.

In the above-described aspect, the container for the medium may have an annulus shape extending around a vertical axis, and the movable stage supports the sample container in movable manner around the vertical axis.

With this configuration, by operating the movable stage to move the sample container around the vertical axis in a state in which the immersion objective lens, which retains the first immersion medium under the medium container, is not moved relative to the medium container, and in which the bottom surface of the sample container is soaked in the second immersion medium accommodated in the medium container, the sample container can be horizontally moved to place the different positions of the sample container on the optical axis of the immersion objective lens, and therefore a sequential observation can be performed. By forming the medium container in a annulus shape, it becomes possible to perform sample observations sequentially at the same position only by moving the sample container in one direction.

Also, in the above-described aspect, a first medium supply portion that supplies the first immersion medium to the gap between the immersion objective lens and the medium container may be employed.

With this configuration, when the first immersion medium is reduced by drying and the like, it is possible to supply the first immersion medium and then replenish the gap between the immersion objective lens and the medium container by operating the first medium supply portion.

Also, in the above-described aspect, a second medium supply portion that supplies the second immersion medium to an inside of the medium container may be employed.

With this configuration, when the second immersion medium is reduced by drying and the like, it is possible to supply the second immersion medium and then replenish the medium container by operating the first medium supply portion.

Also, in the above-described aspect, a container stage that supports the medium container in a horizontally movable manner with respect to the immersion objective lens may be employed.

With this configuration, it is possible to move the sample container in the medium container relative to the immersion objective lens by horizontally moving the medium container relative to the immersion objective lens by means of the operation of the container stage. By this, it becomes possible to broaden the observation area for the specimen in the sample container. It is assumed that the sample container moves in the medium container, thereby the liquid shortage of the first immersion medium is prevented.

Also, another aspect of the present invention provides an inverted microscope system comprising: the inverted microscope according to any of claims 1 to 5, and the sample container that is capable of accommodating the specimens at different positions along a moving direction by the movable stage.

According to this aspect, the observation of the specimen through the immersion objective lens is performed in a state in which at least the bottom surface of the sample container for accommodating the specimen is soaked in the second immersion medium in the medium container which accommodates the second immersion medium, and in which the first immersion medium is retained between the bottom surface the medium container and the immersion objective lens which is located near the lower side of the medium container.

When the specimens are located at the different positions in the sample container, the sample container is horizontally moved in the medium container by operating the movable stage. When the sample container is horizontally moved relative to the medium container, the state in which the gap between the both containers is filled with the second immersion medium is kept unchanged. Further, since the medium container is not moved relative to the immersion objective lens, the first immersion medium that fills the space therebetween is not largely reduced. Therefore, when the sample container is moved to observe the specimens that are placed at the different positions, it is possible to perform a stable observation for a long time period, preventing liquid shortage of the immersion medium, without a frequent supply of the medium.

In the above-described aspect, the sample container may be a multi-well container that has a plurality of wells which are arranged at intervals along the moving direction by the movable stage and each of which is capable of accommodating a specimen.

By employing this configuration, it becomes possible to perform observation by sequentially positioning the specimens accommodated in the plurality of wells on the optical axis of the immersion objective lens by moving the sample container, which is made of the multi-well container, in the medium container by means of operation of the movable stage.

Also, in the above-described aspect, the sample container may be a plurality of cuvettes that are arranged at intervals along the moving direction by the movable stage and each of which is capable of accommodating a specimen.

With this configuration, it becomes possible to perform observation by sequentially positioning the specimens accommodated in the cuvettes on the optical axis of the immersion objective lens by moving the sample container, which is made of the plurality of cuvettes, in the medium container by means of operation of the movable stage.

Also, in the above-described aspect, the sample container may include a multi-well container that has a plurality of wells which are arranged at intervals along the moving direction by the movable stage, and a plurality of cuvettes which are inserted in the plurality of wells, respectively, and which accommodate a third immersion medium having a refractive index that is the same as or similar to that of the first immersion medium, and also each of which is capable of accommodating a specimen.

By employing this configuration, it becomes possible to perform observation by sequentially positioning the specimens accommodated in the cuvettes on the optical axis of the immersion objective lens by moving the sample container, which is configured so that the cuvettes accommodating the specimens are inserted in the wells accommodating the third immersion medium, by means of operation of the movable stage.

Also, in the above-described aspect, a control unit that controls the movable stage to arrange, on an optical axis of the immersion objective lens, the specimens that are placed at the different positions along the moving direction by the movable stage may be employed.

With this configuration, the movable stage is controlled by operation of the controller, and therefore it becomes possible to perform observation by sequentially positioning the specimens placed at different positions in the sample container on the optical axis of the immersion objective lens.

ADVANTAGEOUS EFFECTS OF INVENTION

The aforementioned aspects afford an advantage of improving the observation reliability, reducing the amount of the immersion medium to be stocked and the frequency of replenishment, and also effectively preventing liquid shortage.

REFERENCE SIGNS LIST 1 inverted microscope system
2 inverted microscope
3 sample container
3a bottom surface
4 movable stage
5 medium container
5a opening portion
5b bottom surface
6 fixed stage (container stage)
7 immersion observation lens
15a, 15b, 15c, 15d well
18, 19 nozzle (first medium supply portion, second medium supply portion)
30 multi-well container (sample container)
31 cuvettes (sample container)
A immersion liquid (first immersion medium)
B immersion liquid (second immersion medium)
C immersion liquid (third immersion medium)
T center axis (vertical axis)
X specimen

The invention claimed is:

1. An inverted microscope system comprising:
an immersion objective lens;
a medium container which is disposed above the immersion objective lens with a gap, wherein the medium container has a bottom surface facing the immersion objective lens and having a transparent portion;
a first immersion medium retained between the immersion objective lens and the bottom surface of the medium container;
a second immersion medium stored in the medium container;
a sample container including a plurality of sample containing portions, each of the plurality of sample containing portions being configured to accommodate a sample, and each of the plurality of sample containing portions having a transparent portion at least in a part of a bottom surface thereof; and
a movable stage which supports the sample container in the medium container such that a gap is provided between the bottom surface of the medium container and the bottom surfaces of the sample containing portions, and which moves the sample container in a horizontal direction relative to the medium container, wherein the sample containing portions are arranged along a moving direction in which the sample container is moved relative to the medium container by the movable stage.

2. The inverted microscope system according to claim 1, wherein:
the medium container has an annulus shape extending around a vertical axis, and
the movable stage supports the sample container in a movable manner around the vertical axis.

3. The inverted microscope system according to claim 1, further comprising a first medium supply portion that supplies the first immersion medium to the gap between the immersion objective lens and the medium container.

4. The inverted microscope system according to claim 1, further comprising a second medium supply portion that supplies the second immersion medium to an inside of the medium container.

5. The inverted microscope system according to claim 1, further comprising a container stage that supports the medium container in a horizontally movable manner with respect to the immersion objective lens.

6. The inverted microscope system according to claim 1, wherein the sample container is a multi-well container that has a plurality of wells which are arranged at intervals along the moving direction, wherein each of the sample containing portions comprises one of the wells.

7. The inverted microscope system according to claim 1, wherein the sample container comprises a plurality of cuvettes that are arranged at intervals along the moving direction by the movable stage, wherein each of the sample containing portions comprises one of the cuvettes.

8. The inverted microscope system according to claim 1, wherein the sample container includes a multi-well container that has a plurality of wells which are arranged at intervals along the moving direction by the movable stage, and a plurality of cuvettes which are inserted in the plurality of wells, respectively, wherein the wells accommodate a third immersion medium, and wherein each of the sample containing portions comprises one of the wells and one of the cuvettes.

9. The inverted microscope system according to claim 1, further comprising a control unit that controls the movable stage to arrange, on an optical axis of the immersion objective lens, the sample containing portions that are placed at different positions along the moving direction by the movable stage.

10. The inverted microscope system according to claim 1, wherein the second immersion medium has a refractive index which is the same as or similar to that of the first immersion medium.

11. The inverted microscope system according to claim 8, wherein the third immersion medium has a refractive index which is the same as or similar to that of the first immersion medium.

* * * * *